Figure 1:
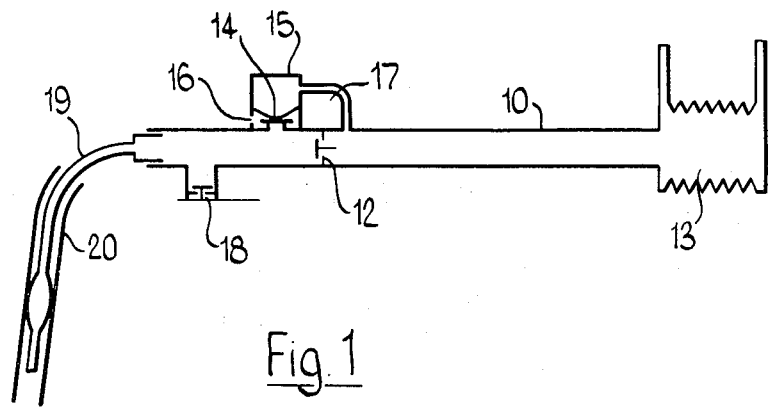

United States Patent [19]

Hammerton-Fraser

[11] 4,316,458
[45] Feb. 23, 1982

[54] PATIENT VENTILATORS
[75] Inventor: Allan M. Hammerton-Fraser, Farnham, England
[73] Assignee: National Research Development Corporation, London, England
[21] Appl. No.: 37,519
[22] Filed: May 8, 1979
[30] Foreign Application Priority Data
  May 9, 1978 [GB] United Kingdom ............... 18539/78
[51] Int. Cl.³ ............................................ A61M 16/00
[52] U.S. Cl. .......................... 128/205.24; 128/207.15; 128/205.13
[58] Field of Search ....................... 128/205.13, 205.14, 128/205.15, 205.16, 205.24, 203.28, 207.15

[56] References Cited
U.S. PATENT DOCUMENTS
2,834,339  5/1958  Bennett et al. ................. 128/205.13
2,841,142  7/1958  Hay ................................ 128/205.13
3,368,555  2/1968  Beasley .......................... 128/204.24
3,993,059 11/1976  Sjostrand ....................... 128/205.13

Primary Examiner—Henry J. Recla
Attorney, Agent, or Firm—Cushman, Darby & Cushman

[57] ABSTRACT

The present invention relates to a delivery tube array which is used to connect a patient to a patient ventilator. A problem arising in such use of patient ventilators is that exhaled air cannot be exhausted directly to the atmosphere since a normal outlet valve would also serve to exhaust air delivered on the compression stroke of the ventilator. The invention overcomes this problem by the introduction into a delivery tube array of a relief valve, a non-return valve 12 and a bleed-pipe which connects the relief valve to a point up-stream of the non-return valve. Such an arrangement ensures that the relief valve opens only when the pressure within the patient's lungs is greater than the pressure upstream of the non-return valve.

7 Claims, 2 Drawing Figures

U.S. Patent

Feb. 23, 1982

4,316,458

PATIENT VENTILATORS

The present invention relates to patient ventilators and is particularly concerned with a delivery tube array used to connect a patient to a patient ventilator.

A patient ventilator is a positive pressure regulator having a reciprocating pump, usually of the bellows type, which is used to maintain or assist the breathing of a paralysed or semi-paralysed patient.

In a respiratory cycle of the ventilator's operation a compression stroke of the bellows pump is arranged to inflate a patient's lungs, while a suction stroke thereof fills the bellows with new respirable gas while the patient's lungs are permitted to deflate. In known ventilators, valve apparatus and the delivery tube array are arranged to permit exhaled air to be exhausted to atmosphere or to testing apparatus by-passing the bellows pump.

The delivery tube of current ventilators normally includes an intermittent mandatory inlet valve which is a non-return valve sited as close to the patient interface as possible and arranged to prevent exhaust therethrough and to permit atmospheric air readily to be drawn into the delivery tube whenever desired. Thus a patient is permitted to inhale whenever he wishes. The valve may be coupled to an oxygen supply having additionally air entrainment means.

It has been observed that as patients begin to recover consciousness they require to cough to clear the excess mucus which has formed on the walls of their lungs. This coughing is apt to be frequent and random. If it occurs on the ventilator compression stroke the pressure peak which results from the coughing reacts against ventilator compression increasing the pressure of the air in the lungs above a tolerable level. This pressure increase may on occasions be sufficient to burst the lungs of a patient. The latter is particularly disturbing because it is most likely to occur when a patient who has been in a paralysed condition for a considerable period, perhaps for more than a week, is showing signs of recovery.

Existing ventilator systems require separate inlet and exhaust tubes, yoked together, to be connected to the final delivery tube as close to the patient as possible, in order to prevent accumulation of an excess of exhaled carbon dioxide in the delivery tube. The weight of this double tube and yoke drags on the final delivery tube.

This problem cannot be overcome by the use of a simple expiratory valve in the delivery tube since such a valve would open on the compression stroke of the ventilator.

The present invention provides a ventilator delivery tube array wich reduces the high pressure increase caused by coughing and allows a single delivery tube to be substantially cleared of exhaled air. Further it prevents the return of exhaled air to the ventilator and thereby reduces contamination of the ventilator by infective agents from the patient.

According to the present invention a delivery tube array for a patient ventilator comprises a gas delivery tube adapted in use to couple a patient to a patient ventilator, a non-return valve within the delivery tube operable to be open during the ventilator compression stroke and to be closed during the ventilator suction stroke, a relief valve in an outlet vent to the delivery tube and positioned downstream of the non-return valve, an air bleed pipe communicating between the relief valve and the upstream of the non-return valve so as to provide a back-pressure to the relief valve whereby, in use the relief valve opens when the gas pressure within the patient's lungs is greater than the gas pressure upstream of the non-return valve and closes when the gas pressure upstream of the non-return valve is equal to or greater than the gas pressure within the patient's lungs. The non-return valve, the relief valve and the bleed-pipe may be produced in the form of an integral unit adapted in use to be coupled to a delivery tube.

In preferred embodiments of the invention the valvery of a delivery tube is all incorporated into a single valvery member. This confers the advantages of interchangeability, readily encapsulable packaging and storage, and disposability. Such a valvery member preferably may have readily identifiable outlet and inlet ends which cannot be incorrectly connected to the delivery tube. Whether such a valvery member is employed or not, having the non-return valve as close to the interface means and as remote from the ventilator as possible may serve to reduce the number of times any of the ventilator apparatus upstream of the non-return valve needs to be sterilised.

Figure 2:
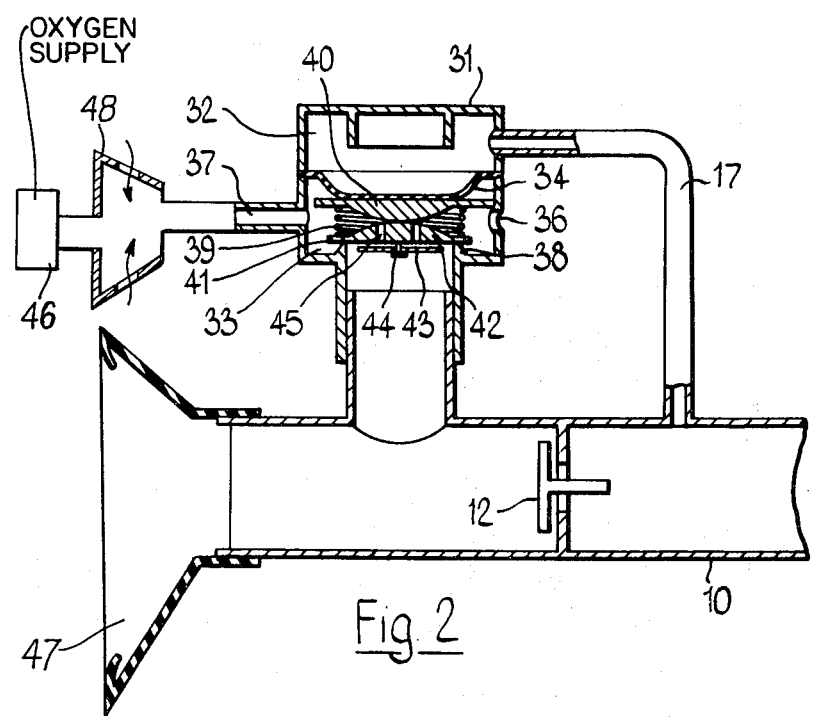

According to an important feature of the present invention the delivery tube array may include an inlet non-return valve in an inlet vent thereto located downstream of the first said non-return valve and operable to open to allow gas to enter the delivery tube via the inlet vent when the pressure within the patient's lungs drops below a pre-determined level. The inlet non-return valve and the relief valve may be part of a composite valve device in a common vent. The inlet vent may be associated with a supply of oxygen and may include air entrainment means as is illustrated in FIG. 2 whereby ambient air is drawn into the vent by the flow of the oxygen.

According to a further feature of the present invention the delivery tube array may include an interface member for linking the delivery tube to the patient and communicating it with the lungs of the patient. The interface member may be an intubating tube for example of the type having a collar inflatable against the trachea to anchor the member and seal the connection. Or it may be a tracheotomy tube or a pressure breathing mask as is illustrated in FIG. 2. A suitable breathing mask is of the oro-nasal type and is substantially constructed of transparent plastics material, such as silicone rubber. If such a mask has a reflected edge seal one mask shape in a limited size range can be adequate for all patients and a minimum of pressure may be required to retain it on a patient's face. As intubation is apt to require a certain skill in its application the mask form of interface member may be preferred in certain situations, for example large scale accidents where several pulmonary casualties may require ventilation at the same time. In such situations the application of mask interface members can be carried out quickly by non-specialist personnel.

In a further preferred form of the present invention the delivery tube array may be substantially constructed from plastics material of low density to reduce the loading at the interface member and thereby minimise the discomfort of the patient. The lightweight aspect of the delivery tube array is particularly important when a patient is connected to a ventilator for a period of several days. Where possible the plastics material should be transparent so that internal operation of the delivery tube array may be observed, and the position of any valve malfunction or pipe blockage quickly located.

According to an aspect of the present invention a patient ventilator includes a delivery tube array in any one of the forms previously described.

A delivery tube array in accordance with the present invention will now be described by way of example with reference to the follwing drawings of which:

FIG. 1 is a schematic diagram of the delivery tube array as used to couple a patient to a ventilator and operating on the ventilator compression stroke, and FIG. 2 shows a composite valve device combining the inlet vent non-return valve and relief valve and operating on the ventilator compression stroke.

The delivery tube array as shown in FIG. 1 includes a delivery tube 10. The delivery tube 10 has wholly mounted therein a non-return valve 12 which is operable to permit air to flow from a bellows type ventilator 13 to the lungs of the patient but to prevent air from flowing from the patient's lungs to the ventilator.

A relief valve 14 is slidably mounted within a chamber 15 and is operable to vent the air in the delivery tube 10 to the atmosphere as required through an opening 16 at the base of the chamber 15. A bleed-pipe 17 has an input end coupled to the chamber 15 and a take-off end coupled to the delivery tube 10 at a position upstream of the non-return valve 12, so that air from the delivery tube 10 may be bled into the chamber 15.

An inlet non-return valve 18 is mounted to the delivery tube 10 at a position downstream of the non-return valve 12. The inlet valve 18 is operable to open when the pressure in the patient's lungs drops below a required level so that ambient air, or oxygenated air from a supply source may be vented into the delivery tube 10.

The delivery tube 10 has one end attached to an interface member such as intubating tube 19, positioned in the trachea 20 of a patient, and the other end attached to the ventilator 13 which receives air of the correct oxygen content from an associated air/oxygen supply. The interface member may also be a pressure breathing mask 47 as is illustrated in FIG. 2.

The operation of the apparatus when associated with a paralysed patient will now be described. During the compression stroke of the ventilator 13 air is pumped via the delivery tube 10 into the patient's lungs. While the ventilator is operating normally on the compression stroke the relief valve 14 is prevented from opening because of the increased back pressure in the chamber 15.

On the suction stroke of the ventilator 13 the non-return valve 12 closes and the ventilator 13 refills with clean air. The back pressure in the chamber 15 correspondingly falls. Consequently the elastic recoil of the diaphragm and of the chest wall expels air from the lungs, this leaves the array through the relief valve 14.

If a patient begins to emerge from a paralysed condition his automatic breathing response may not be synchronised with the breathing sequence of the ventilator. If the patient commences to inhale on the ventilator suction stroke the inlet non-return valve 18 opens and allows air to flow from the atmosphere into the lungs of the patient. Should this not occur the patient would be deprived of needed air. If the patient coughs during a compression stroke the non-return valve 12 closes. As a result the pressure on the relief valve 14 is greater than the back pressure acting thereon in the chamber 15 and the relief valve 14 opens to allow the air discharged from the lungs to be vented to the atmosphere through the opening 16.

In a modified form of the delivery tube array, the relief valve 14 may be combined with the inlet non-return valve 18 to form a combined valve device as shown in FIG. 2. The composite valve device comprises a casing 31 which is divided into an upper chamber 32 and a lower chamber 33 by a deformable membrane 34.

The upper chamber 32 communicates with the delivery tube 10 up-stream of the non-return valve 12 by means of the bleed pipe 17.

The lower chamber 33 is vented to the atmosphere at an aperture 36 and may be coupled to an oxygen supply by means of a projecting tube 37. The lower chamber 33 also communicates with the delivery tube 10 downstream of the non-return valve 12 and includes a valve seating 38. Contained within the lower chamber 33 is a compression spring 39 which is positioned between a pressure plate 40 and a compound valve 41. The compound valve 41 includes a valve plate 42 and a flap-valve member 43 which is centrally mounted to the valve plate by means of a spigot 44. The valve plate 42 has a domed upper face and a series of annular holes 45 therein.

In operation of the composite valve device, air compressed by the ventilator enters the upper chamber 32 and expands downwardly the deformable membrane 34 which acts in turn against the pressure plate 40 to depress the valve plate against the valve seating 38.

If the pressure of the air at the upstream side of the nonreturn valve 12 is greater than or equal to that at the downstream side, then the valve plate 42 will remain closed against the valve seating 38 preventing the release to atmosphere of the air within the delivery tube. In this condition the holes 45 are closed by the flap valve member 43.

When the ventilator is operating on its suction stroke the force exerted by the membrane is considerably reduced and any pressure which is marginally higher than atmospheric is sufficient to lift open the valve plate 42 from the seating 38 allowing a patient to exhale.

When on the ventilator compression stroke the pressure at the downstream side of the non-return valve is higher than at the upstream side, as occurs when the patient coughs, the valve plate 42 will open and the discharged air released to the atmosphere through the aperture 36. The flap valve member 43 is operable to uncover the holes 45 whenever the pressure within the delivery tube, at the downstream side of the non-return valve 12 is less than the atmospheric pressure. Consequently if the patient requires to inhale on the suction stroke of the ventilator the pressure drop induced by the inhaling action causes the flap valve member 43 to uncover the holes 45 and allow air and oxygen into the patient's lungs.

An oxygen entrainment means 48 and oxygen supply 46 may be coupled to the composite valve, the advantage being that during the period when the patient is taking over from the machine his breathing air can readily be enriched without disturbing the apparatus. The construction of the valve tends to ensure entrainment of air and adequate mixing of air aand oxygen.

I claim:

1. A delivery tube array for a patient ventilator usable for delivering a compression stroke and a suction stroke, the delivery tube array comprising:

a gas delivery tube including means adapted in use to couple a patient to the patient ventilator for delivering compression and suction strokes to the patient;

a non-return valve within the delivery tube operable to be open during the ventilator compression stroke and to be closed during the ventilator suction stroke;

a casing having an upper and lower chamber, said lower chamber having an inlet connected to said gas delivery tube downstream of the non-return valve, said lower chamber also having an outlet vent connected to atmosphere;

an air bleed pipe communicating between the upper chamber and the gas delivery tube upstream of the non-return valve;

diaphragm means in said casing for sealing said upper chamber from said lower chamber;

relief valve means in said lower chamber for closing said lower chamber inlet and providing one way flow from said gas delivery tube to said vent;

biasing means operatively associated between said diaphragm means and said relief valve means for holding said relief valve means closed during a suction stroke, said diaphragm means responsive to pressure in said upper chamber during a compression stroke for holding said relief valve means closed during said compression stroke;

an inlet valve means through said relief valve means for providing one way flow from said lower chamber to said gas delivery tube whereby in use the relief valve means opens when the pressure within the patient's lungs is greater than the gas pressure upstream of the non-return valve, and closes when the gas pressure upstream of the non-return valve is equal to or greater than the gas pressure within the patient's lungs, and the inlet valve means is operable to allow gas to enter the delivery tube when the patient attempts to inhale during a suction stroke.

2. A delivery tube array as claimed in claim 1 including an oxygen supply and an air entrainment means connecting said oxygen supply to said outlet vent.

3. A delivery tube array as claimed in claim 2 in which the inlet valve means and the relief valve means are part of an composite valve device.

4. A delivery tube array as claimed in claim 1 which is constructed of low density plastics material.

5. A delivery tube array as claimed in claim 4 in which the plastics material is transparent.

6. A delivery tube array as claimed in claim 1 in which said means adapted to couple a patient to a patient ventilator includes a breathing mask of the oronasal type attached to the delivery tube.

7. A delivery tube array as claimed in claim 6 and wherein the breathing mask has a reflective edge seal.

* * * * *